United States Patent [19]

Zbaida et al.

[11] Patent Number: 4,864,031

[45] Date of Patent: Sep. 5, 1989

[54] PROCESS FOR THE RESOLUTION OF D,L-RACEMIC MIXTURES

[75] Inventors: David Zbaida, Givataim; Edna Shavit, Rehovot; Lia Addadi, Rehovot; Meir Lahav, Rehovot; Isabelle Weissbuch, both of Rehovot, all of Israel

[73] Assignee: Yeda Research and Development Co., Ltd., Rehovot, Israel

[21] Appl. No.: 248,279

[22] Filed: Sep. 22, 1988

[30] Foreign Application Priority Data

Nov. 12, 1985 [IL] Israel ............................. 77031

[51] Int. Cl.⁴ .................. C07D 233/64; C07C 79/46; C07B 62/00
[52] U.S. Cl. ..................................... 548/344; 558/48; 560/22; 562/402
[58] Field of Search ........................ 548/344; 558/48; 560/22; 562/402

[56] References Cited

U.S. PATENT DOCUMENTS

| | | | |
|---|---|---|---|
| 2,790,001 | 4/1957 | Purvis | 558/48 |
| 2,937,200 | 5/1960 | Fike | 558/48 |
| 4,533,506 | 8/1985 | Lahav et al. | 562/402 |

FOREIGN PATENT DOCUMENTS

| | | | |
|---|---|---|---|
| 2458066 | 6/1975 | Fed. Rep. of Germany | 558/48 |
| 3122537 | 3/1982 | Fed. Rep. of Germany | 558/48 |
| 1466150 | 12/1973 | United Kingdom | 548/344 |

OTHER PUBLICATIONS

Addadi et al., J. Am. Chem. Soc., 104 4610, (1982).

*Primary Examiner*—Mary C. Lee
*Assistant Examiner*—J. Richter
*Attorney, Agent, or Firm*—Browdy and Neimark

[57] ABSTRACT

The invention relates to a process for the kinetic resolution of D,L-racemic mixtures of racemates crystallizing as conglomerates. Resolution is effected from supersaturated solutions of these which is carried out in the presence of a polymer bound inhibitor of crystallization of the one form, resulting in the preferred crystallization of the one form, and when the other form is desired - in the presence of such inhibitor for the other form. Amongst racemic mixtures amenable to this process are amino acids. The process can be carried out in a two-compartment device, where the compartments are separated by a membrane which is permeable to the constituents of the racemate, while it is impervious to the polymer-bound inhibitor for the crystallization of one of the racemic forms.

15 Claims, No Drawings

PROCESS FOR THE RESOLUTION OF D,L-RACEMIC MIXTURES

This application is a continuation of application Ser. No. 929,318, filed 11/12/86.

FIELD OF THE INVENTION

The invention relates to a process for the kinetic resolution of D,L-racemic mixtures of racemates which crystallize as conglomerates. The resolution is effected in the presence of a suitable polymeric inhibitor, which consists of a polymer backbone to which there is bound either the D form of the enantiomers (or of a modified compound) when the preferred crystalline form is to be the L-form of the racemate, or an L-form of the enantiomers when the resolved form desired is the D-form. Some of the polymers used for the resolution are novel and form part of the invention. Furthermore, this invention relates to a process of resolution as set out above, where the conglomerate phase is metastable.

BACKGROUND OF THE INVENTION

It has been demonstrated that kinetic resolution of racemates crystallizing in the form of conglomerates can be accomplished by carrying out the crystallization in the presence of small amounts of resolved additives, the stereochemical molecular structure of which resembles that of one of the enantiomers of the said racemic mixture. According to that process the non-polymeric inhibitors were added in rather large quantities (up to 10% wt/wt of racemic mixture). In addition such additives were occluded in the bulk of the precipitating crystals, in typical amounts of 0.5-1.5%. Furthermore, the additive cannot be separated from the precipitating crystals, see U.S. Pat. No. 4,533,506, granted Aug. 6, 1985; see also Addadi et al., J. Am. Chem. Soc., 104 4610 (1982).

In the present invention the use of polymeric inhibitors makes it possible to reduce the quantity of the additive by up to a factor of 10 or more.

The invention relates also to a process of resolution as set out above, where the racemate is provided in adjacent compartments of the resolution cell, separated by a suitable membrane, there being added to the first compartment an inhibitor of D-form crystallization, and to the other compartment an inhibitor of L-form crystallization. The result is that in one compartment essentially pure L-form enantiomer is obtained, and in the other D-form. This is made possible by the fact that contrary to the simple additives used before, the polymeric forms do not pass through such membranes.

The invention also relates to this process of separation where a two-compartment device with a membrane is used and to such separation device for this purpose. Various polymers can be used. As example, the invention is illustrated with reference to certain poly-(N$^\epsilon$-acryloyl-L- or -D-amino acid) and poly-(N$^\epsilon$-methacryloyl-D- or -L-amino acid) as the compounds which are used as inhibitors, the amino acid bound to the polymer being chosen according to the racemate which is to be resolved.

We have found that addition in solution of poly-(N$^\epsilon$-acryloyl-L-lysine) (L-PAL) or poly-(N$^\epsilon$-methacryloyl-L-lysine) (L-PMAL) M.W. or poly-[L-$\alpha$-glutamyl)N-Acryloyl)hydrazide])L-PGAH) with different molecular weights in 0.1-1% wt/wt to a supersaturated solution of D,L-glutamic acid.HCl, (Glu.HCl) brings about a preferred crystallization of D-glutamic acid.HCl (D-Glue.HCl). Similarly, addition of poly-(N$^\epsilon$-acryloyl-D-lysine) (D-PAL) or the methacryloyl analogue or D-PGAH allows the L-glutamic acid to precipitate. Furthermore, we have found that from a supersaturated aqueous solution of D,L-asparagine (Asn) addition of (L-PAL) or (L-PMAL) allows the preferred precipitation of D-asparagine monohydrate, (D-Asn.H$_2$O) and the addition of D-analogue polymers allows the separation of L-asparagine monohydrate (L-Asn.H$_2$O). Similarly, the addition of (L-PAL) or (L-PMAL) in 0.1-1% wt/wt to a supersaturated solution of D,L threonine (DL-Thr), brings about preferred crystallization of D-Threonine (D-Thr). Addition of (D-PMAL) or (D-PAL) leads to preferred crystallization of L-threonine (L-Thr).

Analogously, poly-(N-acryloyl-(p-aminobenzoyl)-D-secphenethylamide) (D-PA-PAB-PHA) allows the preferential crystallization of L-sec-phenethylalcohol as its 3,5-dinitrobenzoate from a racemic mixture. Inclusion of poly-(N-acryloyl-(p-aminobenzoyl)-L-secphenethylamide) (L-PA-AB-PHA) causes the preferred precipitation of the D-form. Analogously, the addition of the poly(P-acrylamido-L-phenyl alanine) (L-PA-PhE) or poly-(acryloxy-L-p-tyrosine) (L-PAO-Tyr) or the corresponding methacryloyl polymers allow the preferential crystallization of D-histidine.HCl.H$_2$O (D-HIS.HCl.H$_2$O) from a racemic mixture both at T>45° C. and T<45° C., where the conglomerate phase is metastable. Further, the addition of poly-(p-acrylamido-D-phenyl alanine) (D-PA-Phe) or poly-(acryloxy-D-p-tyrosine) (D-PAO-Tyr) or the corresponding methacryloyl polymer allows the preferential crystallization of L-histadine.HClH$_2$O from the racemic mixture. Similarly, the addition of (L-PAL) or (L-PA-Phe) or (L-PMAL) or (L-PAO-Tyr) or the corresponding methacryloyl polymers allows the preferential crystallization of D-p-hydroxphenyl-glycine-p-toluenesulphonate (D-pHPGpTS). The addition of any of the same D polymers results in the preferential crystallization of L-pHPGpTS. In a similar way, the addition of poly-(p-acrylamido-L-$\alpha$-methyl-phenyl alanine) or the corresponding methacryloyl polymer allows the preferential crystallization of D-$\alpha$-methyl-DOPA (3,4-dihyroxy-$\alpha$-methyl-phenyl alanine). The addition of any of the same D polymers allows preferential crystallization of L-$\alpha$-methyl-DOPA.

A similar resolution can be effected by using a device comprising two compartments separated by a membrane, provided with means for agitation. The L-type polymer is in one compartment (A) while the D-type polymer is in the second compartment (B). The polymer cannot diffuse through the membrane while the molecules of the substrate equilibrate (diffuse through the membrane).

Our previous patent, U.S. Pat. No. 4,533,506 describes that racemic conglomerates can be resolved by small molecular weight additives. We have now found that soluble polymers are much more efficient and useful. The fact that the additive is chemically bound to a polymer backbone, taking advantage of the cooperative effect, makes it possible to introduce the polymer in the desired solution in a very reduced amount (up to 1% wt/wt) of the racemic mixture to be resolved. In addition the polymer is not occluded in the crystals but remains in solution. Improved resolution, i.e. high chemical and optical yield of the desired enantiomer is achieved. Since the additive is linked to a polymer of high molecular weight, it allows carrying out the resolution of a racemic mixture in a device of two compartments separated by a membrane.

EXPERIMENTAL

This invention can be used to produce crystalline threonine, asparagine.$H_2O$, glutamic acid.HCl, phenethyl alcohol (as its 3,5-dinitrobenzoate), histidine HCl.$H_2O$ and p-hydroxyphenylglycine (as its p-toluenesulphonate salt) enriched in the desired enantiomer, or in its pure enantiomeric form, without requiring the use of seed crystals of this enantiomer. The use of seed crystals of this enantiomer may, however, be desirable from the point of view of the rate of crystallization. For the case where a seed crystal of the desired enantiomer is used, this invention describes an improvement of the process for threonine, asparagine, glutamic acid.HCl, sec-phenethyl alcohol, histidine.HCl.$H_2O$ and pHPGpTS by further addition in solution of the appropriate polymers for each compound. The following examples are illustrative to the present invention but are not to be interpreted in a limiting sense.

EXAMPLES 1–23

Glutamic acid.HCL: D,L glutamic acid (D,L-Glu) (1 g) and poly($N^\epsilon$-acryloyl-L-lysine) or poly-($N^\epsilon$-methacryloyl-L-lysine or poly-[L-glutamyl)N-Acryloyl)hydrazide] were heated in hydrochloric acid 5N (5 ml) at about 60° C. to complete dissolution. The solution was filtered, cooled to room temperature with or without agitation and seed crystals (0.5 mg) of D,L-Glu.HCl added. Crystals formed (20 hrs) were separated by filtration and their enantiomeric excess was determined. The conditions and the results are summarized in Tables I and II.

EXAMPLE 24

An experiment for resolution of D,L-glutamic acid.HCl by a device composed of two compartments separated by a membrane is described. A round perspex piece of 9 cm exterior diameter, 6 cm internal diameter and 0.9 cm thickness was connected to another piece of perspex of the same dimensions via a membrane with cut-off of 10000–15000, and mechanically shaken for 48 h. Into each compartment a solution of 4 g D,L-glutamic acid in 20 ml of HCl 5N was introduced (total 8 g/40 ml). Poly-($N^\epsilon$-acryloyl-L-lysine) or poly-($N^\epsilon$-methacryloyl-L-lysine) was dissolved in one compartment (A) while poly-($N^\epsilon$-acryloyl-D-lysine) or poly-($N^\epsilon$-methacryloyl-D-lysine) was dissolved in the second compartment (B). Each compartment was seeded with 0.5 mg of D,L-glutamic acid.HCl. After 48 h the solid from each compartment was filtered to give from compartment (A) 605 mg of D-glutamic acid.HCl with $(\alpha)D = -24°$ C. and from compartment (B) 575 mg of L-glutamic acid.HCl with $(\alpha)D = +24°$ C.

EXAMPLES 25–29

Asparagine.$H_2O$: A slurry of D,L-Asn.$H_2O$ (500 mg) and poly-($N^\epsilon$-methacryloyl-L-lysine) in water (5 ml) was heated to about 80° C. until complete dissolution occurred. The warm solution was filtered and cooled to room temperature without agitation. After 20 h the separated crystals were recovered by filtration and the enantiomeric excess was determined. The conditions and results are summarized in Table III.

EXAMPLES 30–38

Threonine: D,L-Threonine (DL-Thr) and poly-($N^\epsilon$-methacryloyl-L-lysine) or poly-($N^\epsilon$-acryloyl-L-lysine) were heated in water to about 80° C. until complete dissolution occurred. The hot solution was filtered and cooled to room temperature. After a defined time the precipitate was filtered and the enantiomeric excess was determined. The conditions and results are summarized in Table IV.

EXAMPLE-39–48

3,5-Dinitro-sec-Phenethyl Benzoate: A solution of 3,5-dinitro-DL-sec-phenethylbenzoate in toluene and a solution of poly-(N-acryloyl-(p-amino-benzoyl)-D-sec-phenethylamide) or the poly-L-analogue in N,N'-dimethyl-formamide were mixed together, heated to complete dissolution, and seed crystals of 3,5-dinitro-DL-sec-phenethylbenzoate (0.5 mg) added. The crystals which were formed were separated by filtration, dried and the enantiomeric excess was determined. The results and conditions are summarized in Table V.

EXAMPLES 49–59

Histidine.HCl.$H_2O$: D,L-His.HCl.$H_2O$ (3.2 g) and the appropriate polymer were slurried in water (5 ml) and the slurry was heated to complete dissolution. The hot solution was filtered and allowed to stand at 50° C. for 20 hrs without agitation. The crystals were collected by filtration and the enantiomeric excess was determined. The results are summarized in Table VI.

EXAMPLES 60–67

Histidine. HCl.$H_2O$: D,L-His.HCl.$H_2O$ (4.0 g) and the appropriate polymer were slurried in water (10 ml) and the slurry was heated to complete dissolution. The hot solution was filtered, cooled to 25° C., seeded and allowed to stand without agitation for 3–7 days. The crystals were collected by filtration and the enantiomeric excess was determined. The results are summarized in Table VII.

EXAMPLES 68–76 pHPGpTS: D,L-pHPGpTS and the appropriate polymer were slurried in 0.5M p-toluenesulfonic acid in water, and the slurry was heated until complete solution occurred. The hot soluton was filtered and allowed to cool to room temperature without agitation. The crystals were collected by filtration and the enantiomeric excess was determined. The conditions and results are summarized in Table VIII.

TABLE I

| Example | type of polymer | weight[*1] (%) of polymer | $[\alpha]D$ degree | precipitated crystals e.e.(%) | chemical[*2] yield % |
|---|---|---|---|---|---|
| 1 | L-PMAL | 3 | −23.3 | 94.7 | 22.5 |
| 2 | " | 3 | −23.7 | 96.3 | 25.2 |
| 3 | " | 2 | −24.2 | 98.4 | 22.0 |
| 4 | " | 1 | −23.2 | 94.3 | 26.6 |
| 5 | " | 1 | −24.0 | 97.5 | 21.6 |
| 6 | " | 1 | −24.2 | 98.4 | 22.0 |
| 7 | " | 0.5 | −23.8 | 96.7 | 20.3 |
| 8 | " | 0.5 | −23.6 | 95.9 | 26.5 |
| 9 | " | 0.1 | −11.8 | 47.9 | 33.6 |
| 10 | " | 0.1 | −10.2 | 41.4 | 37.2 |
| 11 | L-PAL | 3 | −24.0 | 97.5 | 15.3 |
| 12 | " | 1 | −23.8 | 96.7 | 12.5 |
| 13 | " | 0.5 | −23.3 | 94.7 | 16.1 |

(Glu.HCl). The following examples were carried out without agitation:

TABLE I-continued (Glu.HCl). The following examples were carried out without agitation:

| Example | type of polymer | weight*1 (%) of polymer | [α]D degree | precipitated crystals e.e.(%) | chemical*2 yield % |
|---|---|---|---|---|---|
| 14 | " | 0.1 | −23.8 | 96.7 | 11.6 |
| 15 | D-PAL | 0.5 | +22.9 | 93.0 | 15.7 |
| 16 | " | 0.1 | +23.7 | 96.3 | 19.3 |
| 17 | L-PGAH | 1.0 | −23.7 | 96.3 | 18.0 |
| 18 | " | 0.8 | −24.2 | 98.4 | 10.0 |
| 19 | " | 0.5 | −24.2 | 98.4 | 12.0 |
| 20 | D-PGAH | 0.8 | −24.0 | 97.5 | 18.0 |
| 21 | " | 0.5 | −24.2 | 98.4 | 18.0 |

*1 expressed in weight % of racemic glutamic acid. HCl. This same notation (weight % of racemic material is used in all the following tables.
*2 the chemical yield is defined as;
$$\frac{\text{precipitate}}{\text{total racemic mixture}}$$
This same notation is used in all the following tables.

TABLE II

The following experiments were carried out with agitation (magnetic stirring).

| Example | type of polymer | weight (%) of polymer | [α] D degree | precipitated crystals e.e. (%) | chemical yield % |
|---|---|---|---|---|---|
| 22 | L-PMAL | 1 | −24.2 | 98.3 | 20.4 |
| 23 | " | 1 | −24.0 | 97.5 | 22.0 |

TABLE III (Asn.H$_2$O)

| Example | weight % of polymer | [α] D degree | precipitated crystals e.e of | chemical yield % | conditions seeded with 0.5 mg of |
|---|---|---|---|---|---|
| 25 | 0.2 | −4.3 | 14 | 52.2 | DL-Asn.H$_2$O |
| 26 | 1 | −9.0 | 29.5 | 45.0 | DL-Asn.H$_2$O |
| 27 | 2 | −28.3 | 92.7 | 14.6 | D-Asn.H$_2$O |
| 28 | 4 | −12.0 | 39.3 | 40.0 | DL-Asn.H$_2$O |
| 29 | 4 | −27.7 | 90.8 | 15.6 | D-Asn.H$_2$O |

TABLE IV (Thr.) The following experiments were carried out eith D,L seed crystals (0.5 mg):

| Example*' | wt. (gr) of DL-Thr (gr) | Vol. of H$_2$O (ml) | Weight % of Poly-(N—methacryloyl-L-lysine) | time h | [α] D degree | precipitated crystals e.e | chemical yield % |
|---|---|---|---|---|---|---|---|
| 30 | 0.9 | 3 | 3.3 | 20 | +15.0 | 95.3 | 23.1 |
| 31 | 1.5 | 5 | 1.3 | 20 | +26.6 | 94.6 | 27.6 |
| 32 | 0.9 | 3 | 1.1 | 6 | +25.7 | 91.7 | 12.6 |
| 33 | 1.5 | 5 | 1.1 | 20 | +26.9 | 96.0 | 18.4 |
| 34 | 0.9 | 3 | 0.5 | 6 | +25.3 | 90.3 | 10.0 |
| 35 | 0.9 | 3 | 0.5 | 20 | +8.0 | 28.5 | 34.2 |
| 36 | 1.5 | 5 | 0.3 | 20 | +25.8 | 92.1 | 19.0 |
| 37 | 0.9 | 3 | 0.5 | 20 | +22 | 78.5 | 22.2 |
| 38 | 0.9 | 3 | 1 | 20 | +23.9 | 85.3 | 19.6 |

*' Experiments 30-36 were carried out without agitation and experiments 37-38 with agitation.

TABLE V (3,5-Dinitro-D,L-sec-phenethyl benzoate)

| Example | wt. (gr) of DL-substr. | Vol. of toluene (ml) | Vol. of DMF (ml) | Polym config. | Weight (%) of polym | time h | [α] D degree | precipitated crystals e.e. | chemical yield % |
|---|---|---|---|---|---|---|---|---|---|
| 39 | 1.4 | 0.5 | 1 | D | 2 | 5 | +37.5 | 97.4 | 6.4 |
| 40 | 1.5 | 0.5 | 1 | D | 1 | 7.5 | +38.5 | 100 | 10 |
| 41 | 1.5 | 0.5 | 1 | D | 1 | 11 | +33.5 | 87 | 15 |
| 42 | 1.5 | 0.5 | 1.5 | D | 3 | 24 | +38.5 | 100 | 14 |
| 43 | 1.5 | 0.5 | 1 | D | 0.2 | 5 | +5 | 13 | 8.6 |
| 44 | 4.5 | 0.5 | 3 | D | 1 | 8 | +38.5 | 100 | 11.2 |
| 45 | 1.5 | 0.5 | 1 | | None | 3.5 | 0 | 0 | 22 |
| 46 | 1.5 | 0.5 | 1 | L | 1 | 7 | −38.5 | 100 | 9.5 |
| 47 | 1.5 | 0.5 | 1.5 | L | 2 | 18 | −38.5 | 100 | 11 |
| 48 | 1.5 | 0.5 | 1 | L | 1.5 | 6 | −38.0 | 98 | 7 |

TABLE VI (His.HCl.H$_2$O)

| Example | wt % of polymer | type of polymer | polym. config. | seeding with | [α] D degree | precipitated crystals e.e. | chemical yield % |
|---|---|---|---|---|---|---|---|
| 49 | 1 | PA-Phe | L | No | −8.8 | 91.6 | 6.9 |
| 50 | 1 | " | L | D-His.HCl.H$_2$O | −9.6 | 100 | 10 |

TABLE VI-continued (His.HCl.H₂O)

| Example | wt % of polymer | type of polymer | polym. config. | seeding with | [α] D degree | precipitated crystals e.e. | chemical yield % |
|---|---|---|---|---|---|---|---|
| 51 | 1 | " | L | D-His.HCl.H₂O | −9.1 | 94.7 | 11 |
| 52 | 1 | " | D | L-His.HCl.H₂O | +9.6 | 100 | 10 |
| 53 | 1 | PAO—Tyr | L | D-His.HCl.H₂O | −9.6 | 100 | 8.4 |
| 54 | 1 | " | L | D-His.HCl.H₂O | −9.6 | 100 | 8.3 |
| 55 | 1 | " | D | L-His.HCl.H₂O | +9.2 | 95.8 | 8.5 |
| 56 | 0 | — | — | D-His.HCl.H₂O | −0.9 | 9.3 | 11 |
| 57 | 0 | — | — | L-His.HCl.H₂O | +0.8 | 8.3 | 10.3 |
| 58 | 10 | PMAL | L | D-His.Hcl.H₂O | −4.8 | 50 | 19.0 |
| 59 | 10 | PMAL | D | L-His.HCl—H₂O | +5.8 | 50 | 12.0 |

TABLE VII (His.Hcl.H₂O)

| Example | wt % of polymer | type of polymer | Polym. config. | seeding with | [α] D degree | precipitated crystals e.e. % | chemical yield (%) |
|---|---|---|---|---|---|---|---|
| 60 | 2 | PA—Phe | L | D-His.HCl.H₂O | −9.6 | 100 | 15 |
| 61 | 2 | PA—Phe | D | L-His.HCl.H₂O | +9.6 | 100 | 15 |
| 62 | 2 | PAO—Tyr | L | D-His.HCl.H₂O | −9.6 | 100 | 15 |
| 63 | 2 | PAO—Tyr | D | L-His.HCl.H₂O | +9.6 | 100 | 15 |
| 64 | 3 | PA—Phe | L | DL-His.HCl.H₂O | −9.6 | 100 | 13 |
| 65 | 3 | PA—Phe | D | DL-His.HCl.H₂O | +9.6 | 100 | 13 |
| 66 | 3 | PAO—Tyr | L | DL-His.HCl.H₂O | −9.6 | 100 | 13 |
| 67 | 3 | PAO—Tyr | D | DL-His.HCl.H₂O | +9.6 | 100 | 13 |

TABLE VIII (PHPGpTS)

| Example | D L PHpGpTS, gr/ml* | weight % of polym | type of polymer | polym config | seeding with | Time h | [α] degree | precipitated crystals e.e. | chemical yield % |
|---|---|---|---|---|---|---|---|---|---|
| 68 | 0.4/2 | 1.2 | PMAL | L | No | 20 | −65.7 | 97.6 | 13.2 |
| 69 | 0.4/2 | 5 | " | D | No | 20 | +65 | 96.5 | 12.2 |
| 70 | 0.5/2 | 2.5 | " | L | No | 20 | −38.5 | 57.2 | 25.8 |
| 71 | 0.5/2 | 2.5 | " | L | D-PHPGpTS | 20 | −24.0 | 35.7 | 32.4 |
| 72 | 0.5/2 | 2.5 | " | L | " | 20 | −59.7 | 88.7 | 22.8 |
| 73 | 1.4/4 | 1 | PA—Phe | L | " | 2 | −66 | 98.0 | 16.5 |
| 74 | 1.4/4 | 1 | " | D | L-PHPGpTS | 2 | +67.2 | 99.8 | 10.0 |
| 75 | 1.4/4 | 1.5 | " | L | DL-PHPGpTS | 2 | −25 | 37.1 | 27 |
| 76 | 1.4/4 | 1 | " | L | DL-PHPGpTS | 2 | −33 | 49.0 | 21 |

*'A solution of 0.5 N of p-toluenesulfonic acid in water.

We claim:

1. A process for the kinetic resolution of D,L racemic mixtures of compounds crystallizing in the form of conglomerates from supersaturated solutions of same, which comprises effecting the crystallization in the presence of an effective quantity of an inhibitor of the crystallization of one form, chemically bound to a polymer, thus promoting the preferred crystallization of the other form.

2. A process according to claim 1, where the conglomerate form is metastable and the polymer is an inhibitor of the stable racemic form as well.

3. A process according to claim 1, whenever effected in a system comprising two compartments separated by a membrane permeable to the constituents of the racemate, yet impermeable to the polymer-bound moieties, where in one compartment there is located a polymer bound L-inhibitor inhibiting the crystallization of the L-form, and in the other a poly D-analogue inhibiting the crystallization of the D-form.

4. A process according to claim 1, for resolution of a mixture of D-and L-glutamic acid hydrochloride which comprises forming a supersaturated solution of said mixture, adding poly-(N$^\epsilon$-acryloyl-L-lysine) or poly-(N$^\epsilon$-methacryloyl-L-lysine) or poly-[L-2-glutamyl-(N-acryloyl)hydrazide] as an inhibitor of the L-amino acid when D-amino acid is desired, or a similar additive in the D-form when the L-form is desired, and crystallizing part of the desired form from said supersaturated solution.

5. A process according to claim 4, whenever effect in a membrane-separated two-compartment system.

6. A process according to claim 1, for resolution of a mixture of D- and L-forms of asparagine, which comprises forming a supersaturated solution of said mixture, adding poly-(N$^\epsilon$-acryloyl-L-lysine) or poly-(N$^\epsilon$-methacryloyl-L-lysine) as crystallization inhibitor of the L-form of asparagine when the D-form of asparagine is desired, or adding the D-form of one of these polymers when the L-form of asparagine is desired; and crystallizing a part of the desired form of asparagine from said supersaturated solution.

7. A process according to claim 1 for the resolution of a mixture of D- and L- forms of threonine which comprises forming a supersaturated solution of said mixture, adding poly-(N$^\epsilon$-acryloyl-L-lysine) or poly-(N$^\epsilon$-methacryloyl-L-lysine) as a crystallization inhibitor of the L-form of threonine when the D-form of threonine is desired, or adding the D-form of the polymer when the L-form of threonine is desired, and crystallizing a part of the desired form of threonine from said supersaturated solution.

8. A process according to claim 1, for resolution of a mixture of D- and L-histidine HCl which comprises forming a supersaturated solution of said mixture, adding poly-(N$^\epsilon$-acryloyl lysine) or poly-(N$^\epsilon$-methacryloyl-L-lysine) or poly-(p-acrylamido-L-phenyl alanine) or poly-(p-acryloxy-L-tyrosine) as an inhibitor of the crystallization of the L-amino acid when the D-amino acid is desired or an analogous polymeric additive in the D-form when the L-form is desired, and crystallizing part of the desired form of the compound from said supersaturated solution, at a temperature of 45° C. or above.

9. A process according to claim 1, for resolution of a mixture of D- and L-histidine HCl which comprises forming a supersaturated solution of said mixture, adding poly-(p-acrylamido-L-phenyl alanine) or poly-(p-acryloxy-L-tyrosine) as an inhibitor of L amino acid when the D-amino acid is desired or an analogous polymeric additive in D-form when the L-form is desired, and crystallizing part of the compound from said supersaturated solution at a temperature of 45° C. or below.

10. A process according to claim 1, wherein also seed crystals of desired form of His. HCl.H$_2$O are added during the crystallization step.

11. A process according to claim 1 for a resolution of a mixture of D and L-pHPGpTS which comprises forming a supersaturated solution of said mixture, adding poly-(N$^\epsilon$-acryloyl-L-lysine) or poly-(p-acrylamido-L-phenyl alanine) or poly-(p-acryloxy-L-tyrosine) as an inhibitor of the L-amino acid when the D-amino acid is desired, or an analogous polymeric additive in the D-form when the L-form is desired, and crystallizing the desired compound from said supersaturated solution.

12. A process according to claim 1 for resolution of a mixture of D- and L-forms of 3,5-dinitro-sec-phenethylbenzoate, which comprises forming a supersaturated solution of said mixture, adding poly-[N-acryloyl-(p-aminobenzoyl)-D-sec-phenethylamide] or the methacryloyl analog as crystallization inhibitor of the D-form of 3,5-dinitro-sec-phenethylbenzoate when the L-form is desired, or adding the L-form of these polymers when the D-form of 3,5-dinitro-sec-phenethylbenzoate is desired and crystallizing the desired compound from said supersaturated solution.

13. A process in accordance with claim 1, wherein said polymer is a polyacrylic acid or a polymethacrylic acid.

14. A process in accordance with claim 3, wherein said polymer is a polyacrylic acid or a polymethacrylic acid.

15. A process in accordance with claim 1, wherein said D,L racemic mixtures of compounds crystallizing in the form of conglomerates from supersaturated solutions of same is selected from the group consisting of racemic mixtures of D- and L-glutamic acid hydrochloride, D- and L-forms of asparagine, D- and L-forms of threonine, D- and L- histidine HCl, D and L-pHPGpTS and D- and L-forms of 3,5-dinitro-sec-phenethylbenzoate.

* * * * *